US010527402B1

(12) United States Patent
Olsson et al.

(10) Patent No.: US 10,527,402 B1
(45) Date of Patent: *Jan. 7, 2020

(54) PIPE INSPECTION CABLE COUNTER AND OVERLAY MANAGEMENT SYSTEM

(71) Applicant: SeeScan, Inc., San Diego, CA (US)

(72) Inventors: Mark S. Olsson, La Jolla, CA (US); Jan Soukup, San Diego, CA (US); Jeffrey A. Prsha, San Diego, CA (US); Ray Merewether, La Jolla, CA (US)

(73) Assignee: SEESCAN, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/203,485

(22) Filed: Mar. 10, 2014

Related U.S. Application Data

(63) Continuation of application No. 12/766,742, filed on Apr. 23, 2010, now Pat. No. 8,970,211.

(60) Provisional application No. 61/172,142, filed on Apr. 23, 2009.

(51) Int. Cl.
*G01B 7/30* (2006.01)
*G01N 27/82* (2006.01)

(52) U.S. Cl.
CPC .............. *G01B 7/30* (2013.01); *G01N 27/82* (2013.01)

(58) Field of Classification Search
None
See application file for complete search history.

(56) References Cited

U.S. PATENT DOCUMENTS

| 3,579,842 | A | 5/1971 | Scher |
| 3,972,124 | A | 8/1976 | Mikolajczyk |
| 4,400,882 | A | 8/1983 | Thornton |
| 4,718,168 | A | 1/1988 | Kerr |
| 5,084,764 | A | 1/1992 | Day |
| 5,430,665 | A | 7/1995 | Jin et al. |
| 5,474,298 | A * | 12/1995 | Lindsay ............... G01D 5/2033 473/222 |
| 5,546,672 | A | 8/1996 | Campbell et al. |
| 6,505,525 | B2 | 1/2003 | McGrew |
| 6,545,704 | B1 * | 4/2003 | Olsson et al. .................. 348/84 |
| 6,745,487 | B1 | 6/2004 | Nield |

(Continued)

OTHER PUBLICATIONS

"MLX90363 Magnetometer IC with High Speed Serial Interface" by Triaxis, Dec. 2016.*

(Continued)

*Primary Examiner* — Paresh Patel
(74) *Attorney, Agent, or Firm* — Steven C. Tietsworth, Esq.

(57) ABSTRACT

Apparatus for magnetically sensing, computing, and displaying cable distance, as well as computing and displaying other user-selectable information in a pipe inspection system or other system is disclosed. Two or more permanent magnets may be mounted in spaced apart fashion, on either a frame or a rotatable member supported on the frame for rotation about an axis. A magnetic sensor may be mounted on the other one of the rotatable member or frame on which the magnets are not mounted, so that either the magnets rotate around the magnetic sensor or the magnetic sensor rotates between the permanent magnets. The magnetic sensor may generate output signals representing changes in at least two axes in a composite magnetic field generated by the permanent magnets.

16 Claims, 17 Drawing Sheets

(56) References Cited

U.S. PATENT DOCUMENTS

| | | |
|---|---|---|
| 7,235,968 B2 | 6/2007 | Popovic et al. |
| 8,970,211 B1* | 3/2015 | Olsson et al. ............... 324/220 |
| 2005/0024044 A1* | 2/2005 | Poirier ................... G01D 5/246 |
| | | 324/207.25 |
| 2010/0031460 A1 | 2/2010 | Eisermann et al. |

OTHER PUBLICATIONS

"Magnets for MLX90333 Linear Position Sensor" Rev. 1, Aug. 2007.*
"Magnets for MLX90333 Linear Position Sensor" Rev. 2, Aug. 2007.*

* cited by examiner

PIPE INSPECTION CABLE COUNTER AND OVERLAY MANAGEMENT SYSTEM

CROSS-REFERENCE TO RELATED APPLICATIONS

This application is a continuation of and claim priority to co-pending U.S. Utility patent application Ser. No. 12/766,742, entitled PIPE INSPECTION CABLE COUNTER AND OVERLAY MANAGEMENT SYSTEM, filed Apr. 23, 2010, which claims priority under 35 U.S.C. § 119(e) to U.S. Provisional Patent Application Ser. No. 61/172,142, entitled PIPE INSPECTION CABLE COUNTER AND OVERLAY MANAGEMENT SYSTEM, filed Apr. 23, 2009. The content of each of these applications is incorporated by reference herein in its entirety for all purposes.

FIELD

This disclosure relates generally to inspection systems. More specifically, but not exclusively, the disclosure relates to apparatus and methods for measuring the length of cable extending from the reel of a pipe inspection or similar system, as well as to methods of displaying information relating to pipe inspections.

BACKGROUND

Pipe inspection is important in the maintenance of pipe systems such as subterranean waste water drain systems. Traditionally, pipe inspection is accomplished using a camera head attached to the distal end of a semi-rigid push-cable wrapped in turns inside a rotatable drum or reel. The camera head is inserted into the pipe to be inspected and the push-cable is paid out to force the camera head down the pipe. The camera in the camera head sends back still and/or video image signals over conductors embedded in the push-cable. Images of the interior of the pipe generated from the signals are viewed in real time and recorded for later study.

One of the difficulties in pipe inspection is the accurate measurement of the distance the camera head has traveled into the pipe. This information is important in precisely locating blockages or breaks in the pipe. Various techniques have been developed for measuring the distance that a camera head has been pushed down a pipe via a push-cable. For example, U.S. Pat. No. 6,545,704, granted Apr. 8, 2003 to Mark S. Olsson et al., discloses a video pipe inspection system that uses a distance sensing module including two non-contact sensor pairs. U.S. Pat. No. 6,505,525, granted Jan. 14, 2003 to R. Michael McGrew, discloses a sewer pipe inspection system in which a rotor magnet is rotated as a push rod cable is inserted into a pipe. A pair of Hall effect switches are mounted adjacent the rotor magnet and a decoder circuit connected to these switches is used to generate a linear distance traveled by the push rod cable and a footage signal is displayed to the user.

SUMMARY

This disclosure relates generally to inspection systems having deployable cables storable on a cable reel. In one aspect, an apparatus for detecting angular motion about an axis of the cable reel for measuring cable deployment may include a rotatable member, an axle that supports the member for rotation about an axis, and a frame that supports the axle. A magnetic sensor may be mounted on one of the frame and the rotatable member. The magnetic sensor may generate signals representing changes in a magnetic field in at least two axes. Two or more permanent magnets may be mounted in spaced apart relationship on the other one of the frame and rotatable member so that the magnetic sensor can detect changes in a composite magnetic field generated by the permanent magnets during relative rotational movement between the magnetic sensor and the magnets.

Various additional aspects, features, and functionality are further described below in conjunction with the appended Drawings.

BRIEF DESCRIPTION OF THE DRAWINGS

The present disclosure may be more fully appreciated in connection with the following Detailed Description taken in conjunction with the accompanying Drawings, wherein.

DETAILED DESCRIPTION OF EMBODIMENTS

Figure 1A:
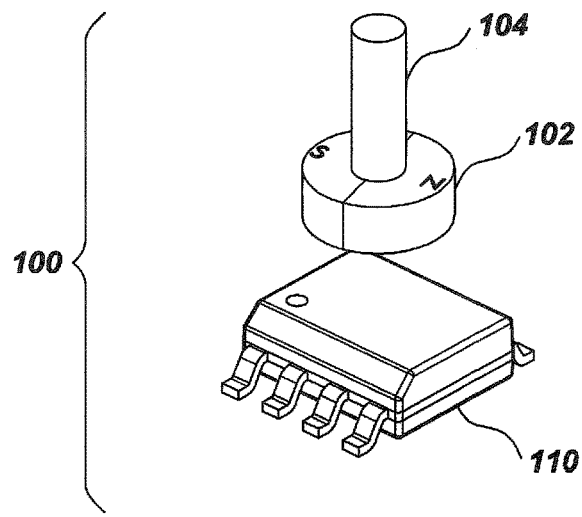
FIG. 1A is an isometric view of a conventional arrangement of a rotating cylindrical permanent magnet adjacent a two-axis magnetic sensor.

Embodiments of the present invention may be used to provide improved methods and apparatus for measuring the distance a pipe inspection camera head has traveled from the reel or drum. Additionally, embodiment of the present invention provide a method and apparatus for labeling images from the pipe inspection camera with labels or diagnostic information for record-keeping or customer informational needs.

One difficulty with the use of a rotor magnet to measure the distance traveled by a push cable paid out from a reel that turns the magnet results from the fact that when using an axle supported at both ends, one cannot readily place a rotating magnet and the sensor along the axis of rotation. It is also often disadvantageous to place the sensor on the outboard end of the axle, outside the support position.

Embodiments of the present invention use a pair of separated cylindrical permanent magnets to form a large, distributed composite magnetic field, and use a magnetic sensor that is sensitive in at least two axes to measure the angle of the magnetic field as the composite magnetic field rotates. The illustrated embodiment of the cable counter of the present invention utilizes a two-axis magnetic sensor such as the MLX90316 commercially available from Melexis. A three-axis magnetic sensor may also be used in place of a two axis sensor. One suitable three-axis magnetic sensor is the MLX90333 commercially available from Melexis. Pages 13 and 14 and FIGS. 3A and 3B of co-pending U.S. patent application Ser. No. 14/756,068 filed Apr. 7, 2010 by Mark S. Olsson et al. entitled "Magnetic Manual User Interface Devices" provide further technical details regarding the Melexis MLX90333 three-axis magnetic sensor. The entire disclosure of the aforementioned co-pending application is hereby incorporated by reference.

In accordance with the present invention, one or more magnetic sensors in a cable handling system measure the composite field formed by a plurality of cylindrical magnets attached to, or embedded into, the surface of a rotatable push-cable storage drum.

Embodiment of the present invention also provide a mechanism for converting the detection by the magnetic sensor into a distance display which can be overlaid onto the camera-view display shown on a monitor, and a means for creating and managing textual overlays to add user-selected information to the visual display as it is recorded for records purposes or for providing better customer information in pipe-inspection operations.

In the preferred embodiment of the present invention, two permanent cylindrical magnets, such as Neodymium magnets, are fixed onto or into a retaining plate to form a composite magnetic field capable of being detected by a proximate two or three-axis magnetic sensor. A neodymium magnet or NdFeB magnet (a variety of rare-earth magnet) is a powerful magnet made of a combination of neodymium, iron, and boron.

A processing unit is configured with parametric settings for the dimension and capacity of the specific pipe inspection cable drum to which the magnet-bearing retaining plate is attached. The processing unit is programmed to compute cable distance based on cable drum revolutions, adjusted for the cable drum size and the increasing diameter of the remaining circular stack of cable within the cable drum as distance paid out increases. Data from the magnetic sensor is processed to produce derivative data including the degree of drum motion, the direction of cable drum motion, and the cable feed rate and feed distance and direction.

In an alternate embodiment, the cylindrical permanent magnets may be embedded into the drum, or otherwise attached. More than two permanent magnets may also be employed. In other embodiments multiple sensors may be incorporated.

FIG. 1A illustrates an example of a conventional magnetic sensor system 100 in which a two axis Hall effect magnetic sensor 110, such as the Sentron/Melexis 2SA-10 sensor, is positioned under a cylindrical permanent magnet 102 attached to a shaft 104. Rotation of the shaft 104 rotates the magnet 102. The magnet 102 is magnetized across its diameter, and when placed in close proximity to the two-axis magnetic sensor 110 it provides an optimal magnetic field shape that is approximately linear (not curved) in the plane of the magnetic sensor 110 which is orthogonal to the axis of rotation of the shaft 104. The rotation of an approximately linear magnetic field shape provides a direct, simple correspondence between the rotation of the shaft 104 and a magnetic field angle measured by the two-axis magnetic sensor 110.

Figure 1B:
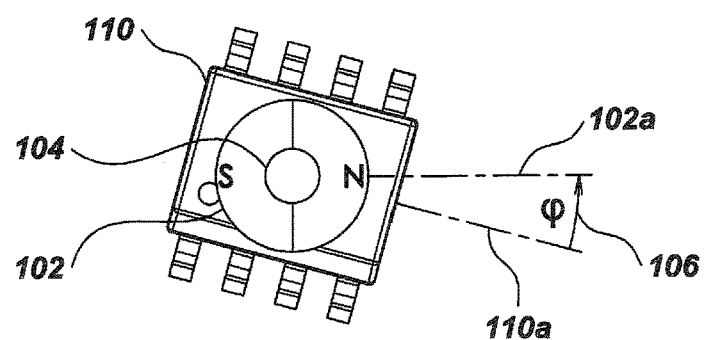
FIG. 1B is a top plan view of the magnet and sensor of FIG. 1A illustrating the angle of Rotation φ.

FIG. 1B diagrammatically illustrates the angle φ between an axis 110*a* of the two-axis magnetic sensor 110 and a magnetic axis 102*a* of the magnet 102 that is measured by the two-axis magnetic sensor 110. The two-axis magnetic sensor 110 is an absolute angle sensor which derives the sine and cosine components of the magnetic field direction from two voltages, $V_x$ and $V_y$, and uses their ratio to determine the angle as the permanent magnet 102 rotates.

In a device with a solid supporting axle, such as a video pipe inspection system, a rotating magnet and sensor arrangement such as magnetic sensor system 100 cannot readily be placed within the axle in order to optimally situate it along the axis of rotation. If the axle is solid, the magnet can be easily knocked off the end of the shaft if mounted in that location.

In accordance with the present invention a composite magnetic field is generated by a plurality of cylindrical permanent magnets, the composite field being approximately centered on the axis of rotation of a push-cable storage drum.

Figure 2:
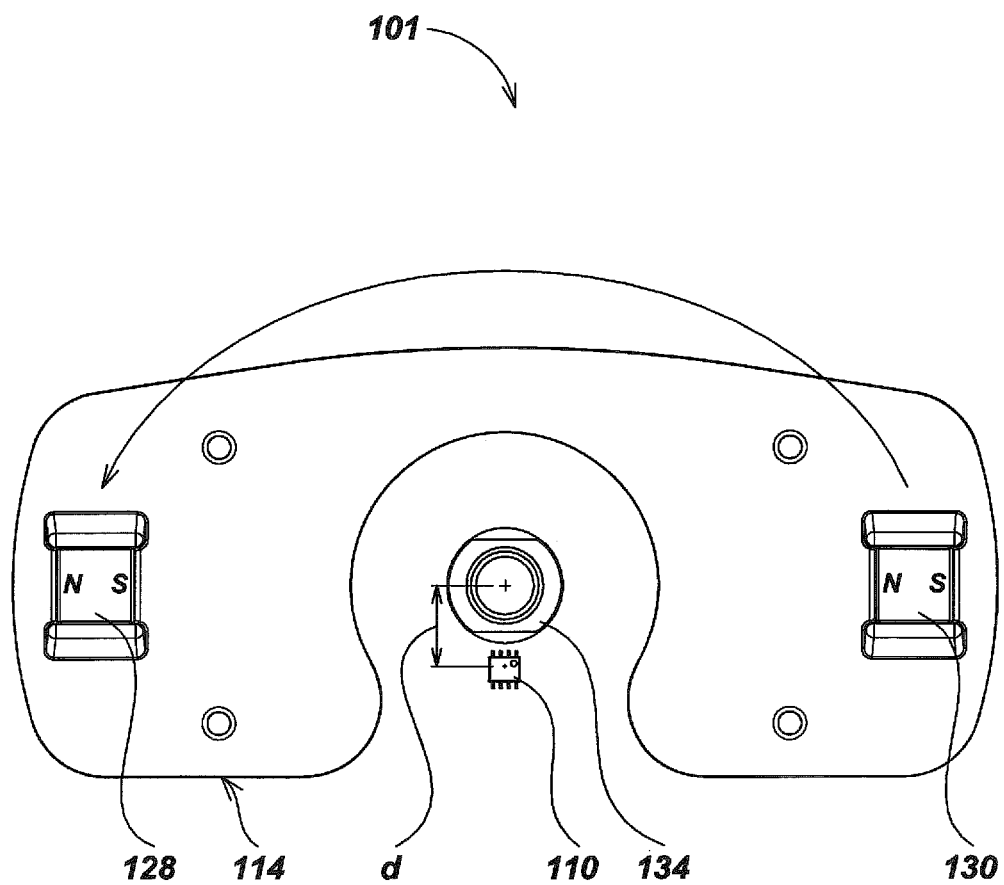
FIG. 2 is a front elevation view of a retaining plate and pair of cylindrical permanent magnets forming part of an embodiment of a cable counter incorporating the present invention.

Referring to FIG. 2, a cable counter assembly 101 includes a plastic retaining plate 114 to which a pair of cylindrical permanent magnets 128 and 130 are operatively attached. The cylindrical permanent magnets 128 and 130 rotate in a counter-clockwise direction around a supporting axle 134 as indicated by the large curved arrow in FIG. 2. A two-axis magnetic sensor 110 is located a predetermined offset distance d below the central axis of the axle 134. The magnetic sensor 110 can be the aforementioned MLX90316 two-axis magnetic sensor commercially available from Melexis that contains Hall-effect devices. The MLX90316 two-axis magnetic sensor is a monolithic integrated circuit (IC) featuring the Triaxis™ sensor developed by Melexis. Conventional Hall effect devices are only sensitive to the flux density applied orthogonally to the surface of the IC. The Triaxis sensor is also sensitive to the flux density applied parallel to the IC surface. The MLX90316 magnetic sensor senses the absolute rotary (angular) position of a diametrically magnetized permanent magnet rotating above it.

The term "permanent magnet" as used herein refers to any object that is magnetized and creates its own persistent magnetic field. Suitable ferromagnetic materials for a permanent magnet include iron, nickel, cobalt, rare earth metals and their alloys, e.g. Alnico and Neodymium. A permanent magnet can also be made of powderized ferromagnetic material held together with an organic binder.

Figure 6:
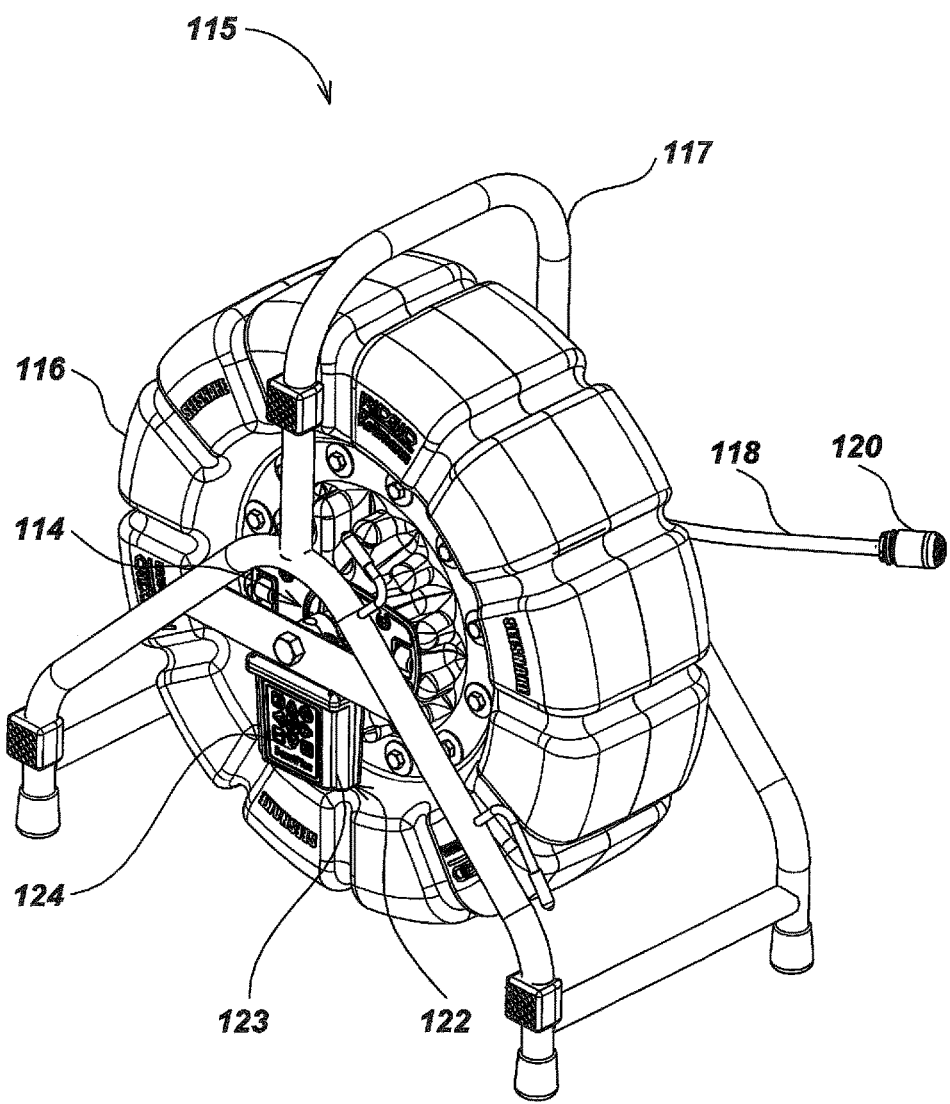
FIG. 6 is an isometric view of a pipe-inspection system including the cable drum assembly and cable counter illustrated in FIG. 5.

The pair of spaced apart magnets 128 and 130 form a larger, distributed composite magnetic field centered on the axis of rotation illustrated diagrammatically in FIG. 2 by the small+sign on the end of the axle 134. The best results are obtained by placing two identical permanent magnets, equidistant from the axis of rotation. The axis running through the two magnets approximately intersects and is approximately perpendicular to the axis of rotation of a rotatable member in the form of a cable storage drum 116 (FIG. 6). The cylindrical permanent magnets 128 and 130 are thus mounted on the cable storage drum 116 and rotate therewith around the stationary magnetic sensor 110. It is desirable to place the magnetic sensor 110 as near as possible to the axis of rotation and to the line running through the two magnets. Proximity to the axis of rotation is limited by the size of the axle, requiring some offset in the placement of the magnetic sensor 110. However such an offset introduces errors in measuring the orientation of the composite magnetic field. The error derives from mounting the sensor 110 away from the axis.

The ability of the magnetic sensor 110 to sense changes in the composite magnetic field generated by the cylindrical permanent magnets 128 and 130 makes it possible to calculate discrete and precise computations of angular rotation. This provides an improved ability to measure precisely the degree of rotation of the cable storage drum 116, and hence compute the extension of a push-cable 118 that is paid out from the cable storage drum 116 as a camera head 120 is pushed down a pipe (not illustrated).

If the diameter of the axle 134 is made larger, the offset d is generally required to be larger. Larger separation between the cylindrical permanent magnets 128 and 130 is also required to maintain small angle-measurement errors. A larger separation of the cylindrical permanent magnets 128 and 130 will also generally require stronger magnets. With error correction, errors resulting from such offset can be largely removed. Errors will become more and more difficult to correct as the errors become larger and larger.

Figure 3:
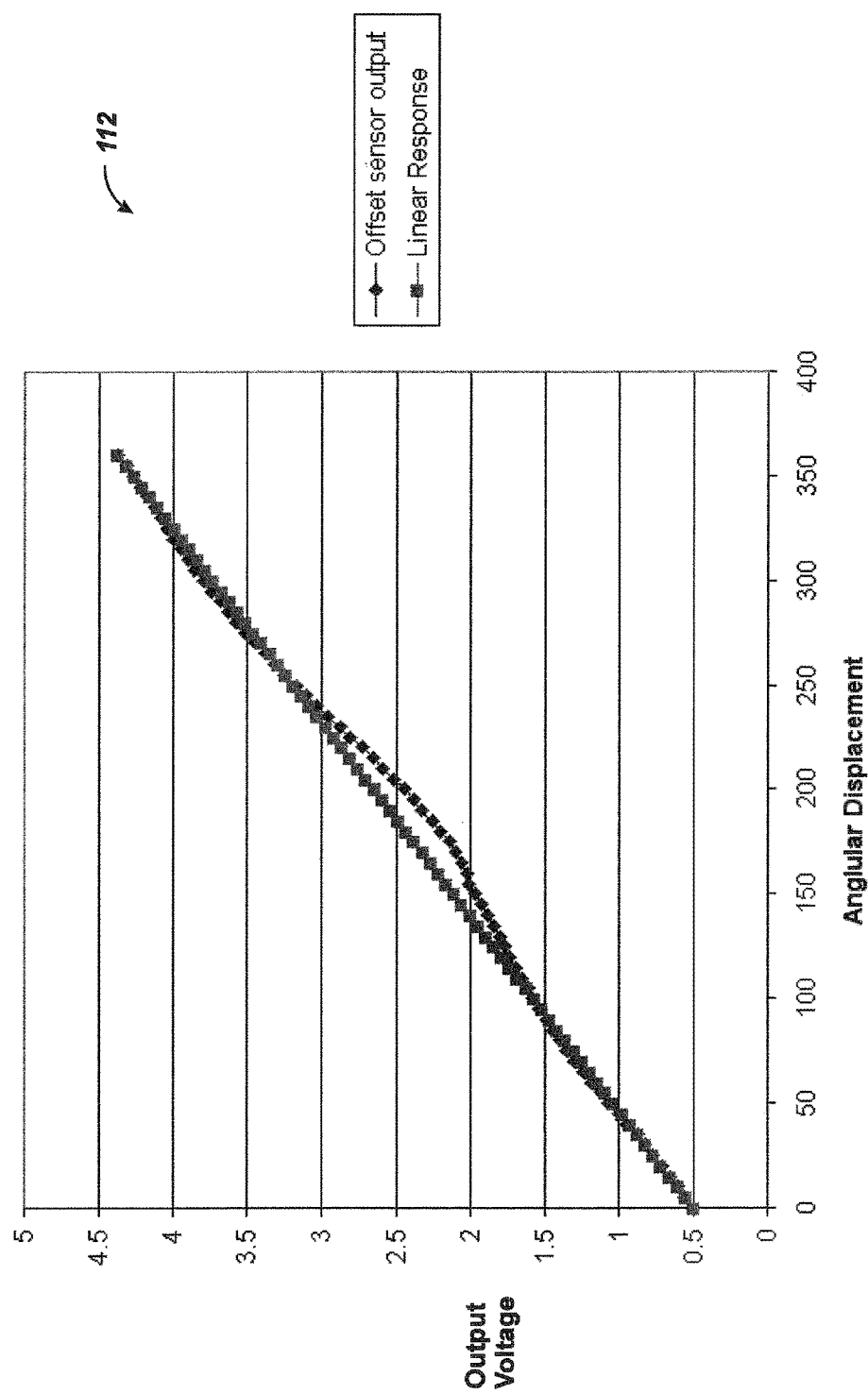
FIG. 3 is a graph illustrating offset errors acquired by testing the cylindrical perm anent magnets and sensor of an embodiment of the cable counter of the present invention when the sensor is offset from the axis of rotation.

FIG. 3 is a graph 112 that illustrates the error introduced by offsetting the two-axis magnetic sensor 110 relative to the axis of rotation as illustrated in FIG. 2. Compared to a linear response, errors in the offset sensor output occur in the region where the angular displacement nears one hundred and eighty degrees. Errors in the opposite direction appear in the regions around seventy five degrees and three hundred degrees of angular displacement. The errors can be corrected in software. For example, a lookup table in memory can be used to associate each measured angle with a corrected value to improve accuracy. Alternatively, a formula derived from a curve fit such as a cubic spline can be used to compute a true angle from the measured field angle.

Figure 4:
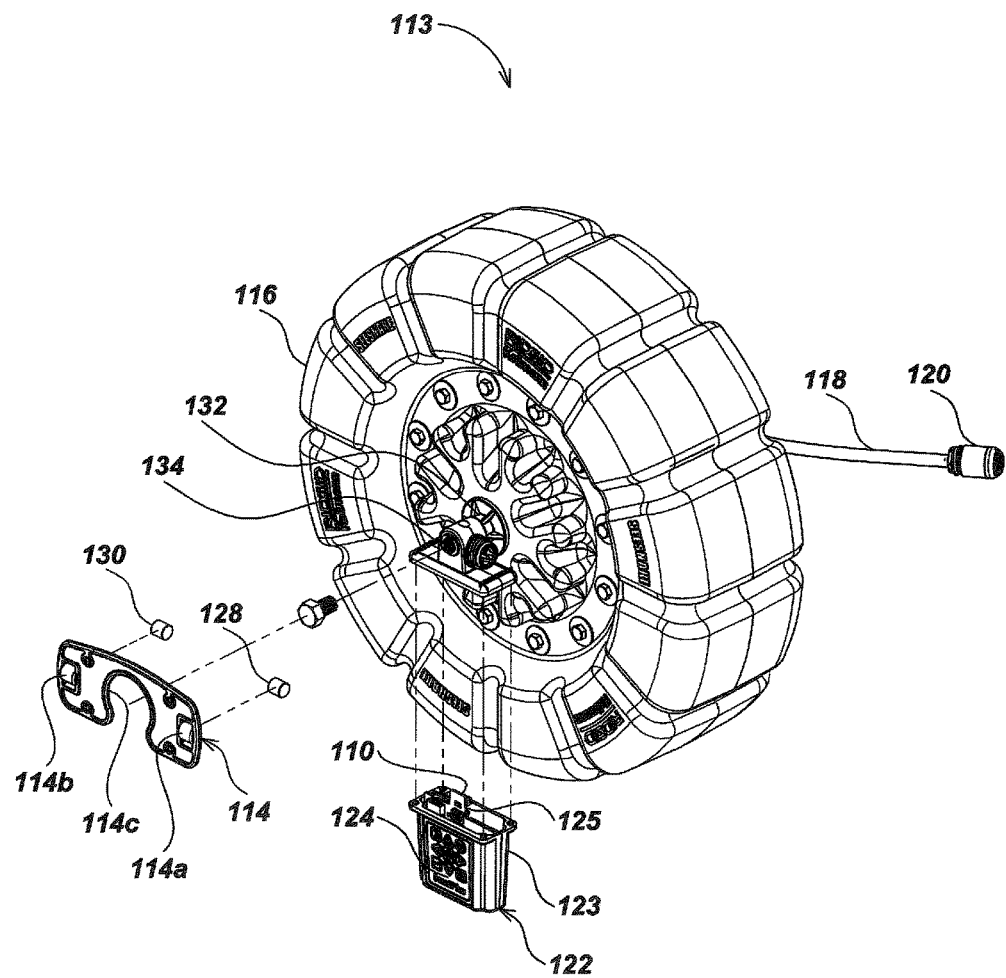
FIG. 4 is a reduced exploded isometric view of a pipe-inspection cable drum assembly equipped with the cable counter components illustrated in FIG. 2.

Referring to FIG. 4, a pipe-inspection cable drum assembly 113 includes the retaining plate 114 that is molded with two pockets 114a and 114b in which the cylindrical permanent magnets 128 and 130 are inserted. A semi-circular cut-away 114c in the retaining plate 114 allows it to rest over a bushing 132 (FIG. 7) on the axle 134 which supports the rotatable cable storage drum 116. The cable storage drum 116 is of molded plastic or similar construction and is designed to hold and constrain the turns of the flexible, resilient push-cable 118 of a pipe inspection system 115 (FIG. 6). The camera head is attached to the distal or leading end of the push-cable 118. The proximal or trailing end of the cable is connected through a slip-ring assembly (not illustrated) for conveying signals to processing circuitry.

One example of a suitable slip-ring assembly is disclosed in U.S. Pat. No. 6,908,310, granted Jun. 21, 2005 to Mark S. Olsson et al., the entire disclosure of which is hereby incorporated by reference. Another example of a suitable slip-ring assembly is disclosed in co-ending U.S. patent application Ser. No. 12/704,808, filed by Mark S. Olsson et al. on Feb. 12, 2010, entitled "Pipe Inspection System with Replaceable Storage Drum." the entire disclosure of which is hereby incorporated by reference. For examples of a suitable push-cable 118 and suitable termination assemblies for coupling the camera head 120 to the push-cable 118 see co-pending U.S. patent application Ser. No. 12/371,540, filed Feb. 13, 2009 by Mark S. Olsson et al., entitled "Push-cable for Pipe Inspection System" the entire disclosure of which is hereby incorporated by reference.

Figure 8:
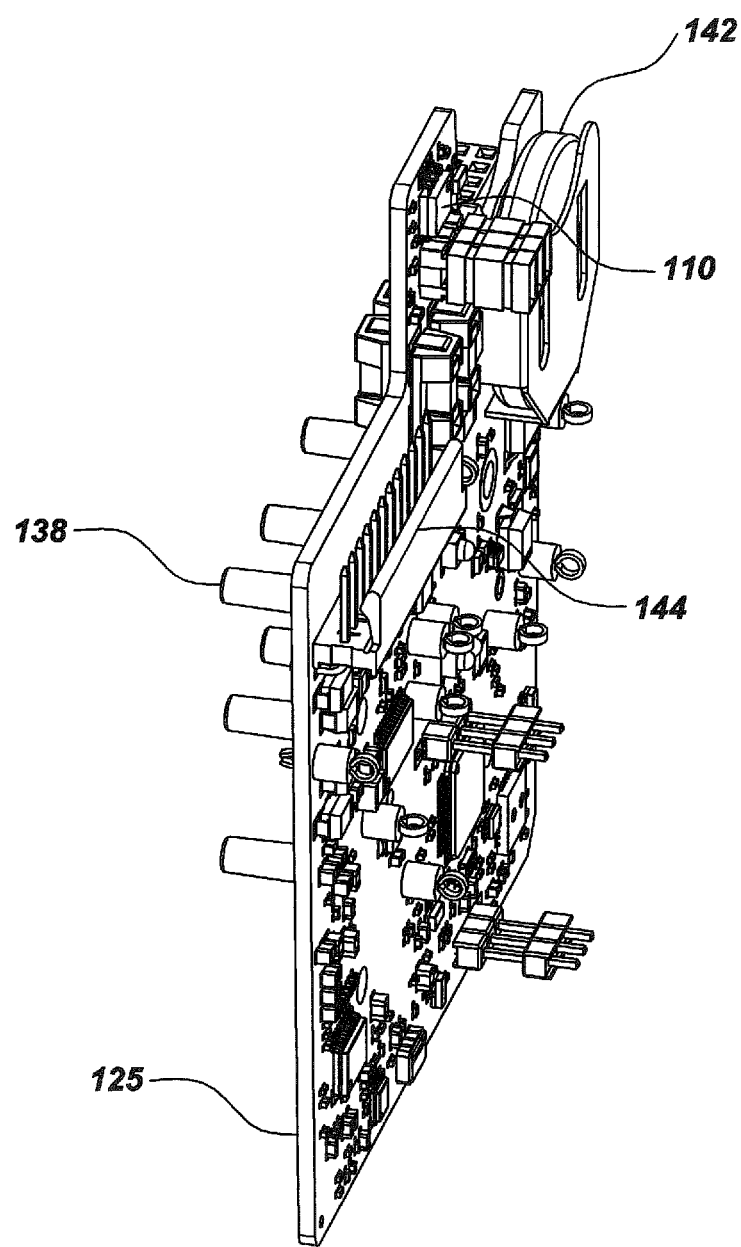
FIG. 8 is an enlarged detailed isometric view of a circuit board assembly that supports the magnetic sensor of the illustrated embodiment of the cable counter.

Referring still to FIG. 4, a counter module 122 includes a user-accessible keypad 124, an outer case 123, and a printed circuit board (PCB) 125 which incorporates the two-axis magnetic sensor 110 and supporting circuitry illustrated in FIG. 8.

Figure 5:
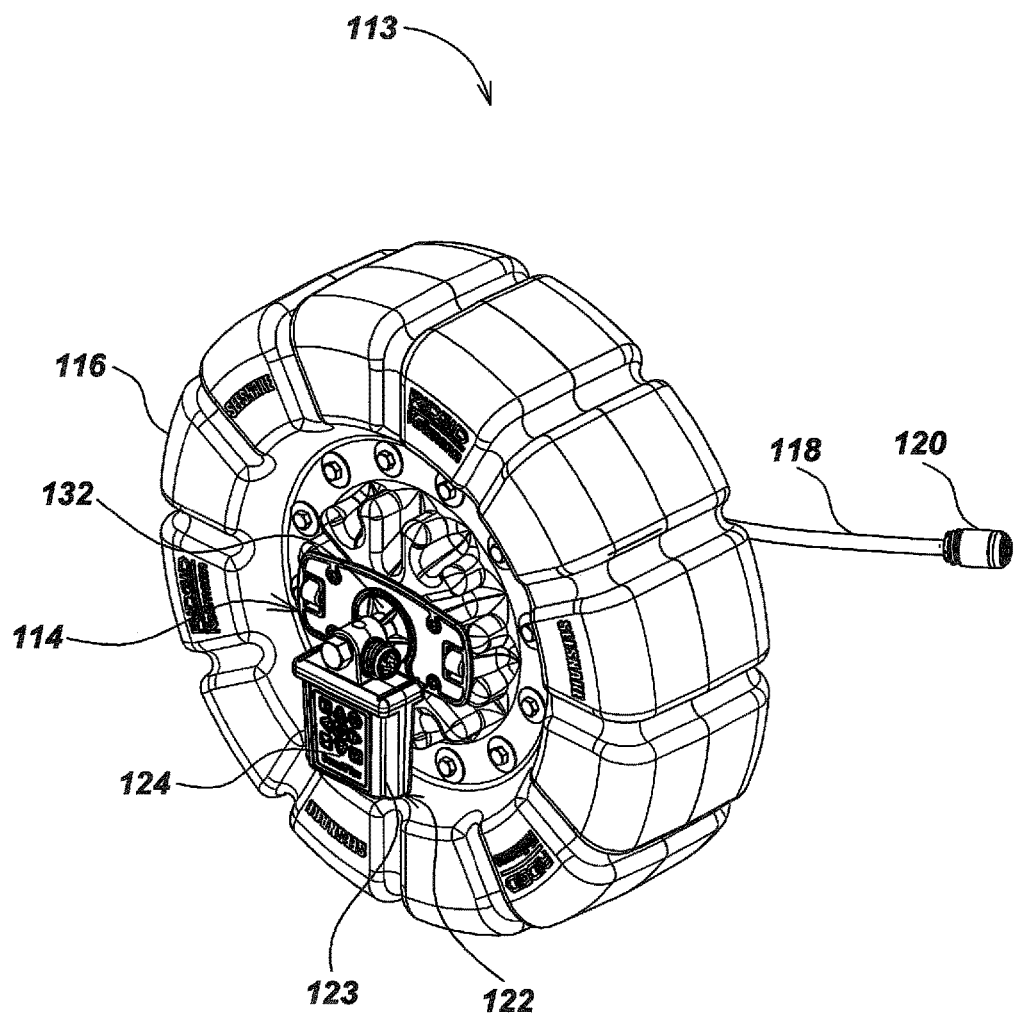
FIG. 5 is an isometric view of the assembled cable drum assembly and cable counter components illustrated in FIG. 4.

Referring to FIG. 5, the retaining plate 114 is assembled over the bushing 132 and attached to the drum 116 for rotation therewith. The counter module 122 is attached to the axle 134 (FIG. 4) and does not rotate with the drum 116, while the retaining plate 114 does rotate with the drum 116.

Referring to FIG. 6 the pipe inspection system 115 includes a tubular metal frame 117 that supports the axle 134 (FIG. 4). The opposite ends of the axle 134 are fixed to the frame so that the axle 134 does not rotate. The axle 134 rotatably supports the cable storage drum 116 as the push-cable 118 is paid out of a central opening in the drum. The cable storage drum 116 rotates about the fixed axle 134. The opening that permits the push-cable to be fed out is not visible in FIG. 6 because it is on the opposite side of the cable storage drum 116. See FIG. 3 of the aforementioned U.S. Pat. No. 6,545,704, the entire disclosure of which is hereby incorporated by reference. The cable storage drum 116 is manually spun when the push-cable 118 is pulled out of the cable storage drum 116 and when the push-cable 118 is fed back into the cable storage drum 116. As the push-cable 118 is fed out of the cable storage drum 116 the camera head 120 is forced down a pipe (not illustrated) that is being inspected. The counter module 122 is attached to the axle 134 (FIG. 4) and is fixed relative to the frame 117.

Figure 7:
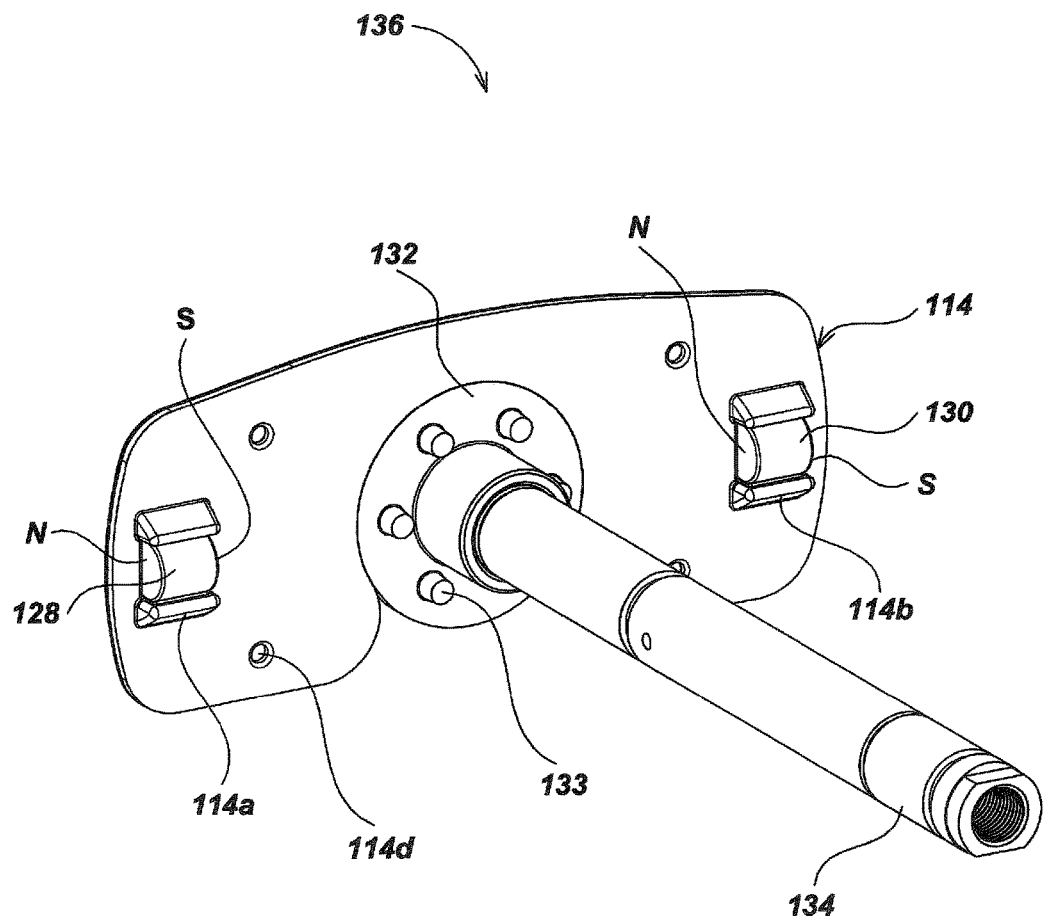
FIG. 7 is a rear isometric view of the retaining plate of FIG. 2 illustrating the location and orientation of the cylindrical permanent magnets and drum support axle.

FIG. 7 illustrates the cylindrical permanent magnets 128 and 130 and the retaining plate 114 in an assembly 136. The cylindrical permanent magnet 130 is oriented horizontally to the right (in this view) of the axle 134, with its North pole toward the axle 134. The cylindrical permanent magnet 128 is oriented horizontally to the left of the axle 134 in a similar orientation with its North pole away from the axle 134. The magnetic axes of the cylindrical permanent magnets are thus aligned and substantially intersect the axis of rotation of the cable storage drum 116. The retaining plate 114 that supports the cylindrical permanent magnets 128 and 130 fits over the bushing 132. The retaining plate 114 is attached to the molded surface of the drum (116 in FIG. 3) with four self-tapping screws (not illustrated) that are inserted through holes 114d and the retaining plate 114 rotates with the cable storage drum 116. The bushing 132 and the retaining plate are both separately mounted to the rotatable cable storage drum 116 but are not attached to each other. The curved edge of the semi-circular cut-away 114c rests against the complementary curved surface of the bushing 132. Six key pins 133 (FIG. 7) fit into corresponding holes (not illustrated) in the cable storage drum 116 that force the bushing 132 to rotate with the cable storage drum 116.

The two-axis magnetic sensor 110 (FIG. 4) within the counter module 122 (FIG. 5) is located and mounted to be fixed relative to the rotation of the cable storage drum 116 (FIG. 5) and its attached retaining plate 114 and the two cylindrical permanent magnets 128 and 130. The combined magnetic fields from the two cylindrical permanent magnets 128 and 130 form a composite magnetic field. The magnetic sensor 110 detects changes in the composite magnetic field resulting from rotation of the cylindrical permanent magnets 128 and 130 around the magnetic sensor 110. The output signal of the magnetic sensor 110 can be processed with pre-programmed firmware or software to accurately determine the degree and amount of rotary motion of the cable storage drum 116 (FIG. 4).

An alternate configuration is equally possible in which the plurality of cylindrical magnets is fixed and the sensor rotates relative to them. The cylindrical magnets, therefore, may be attached to the rotating drum as illustrated in the preferred embodiment, or alternatively on the frame 117 which remains fixed relative to the cable storage drum 116, with the magnetic sensor 110 attached to the cable storage drum.

Figure 9:
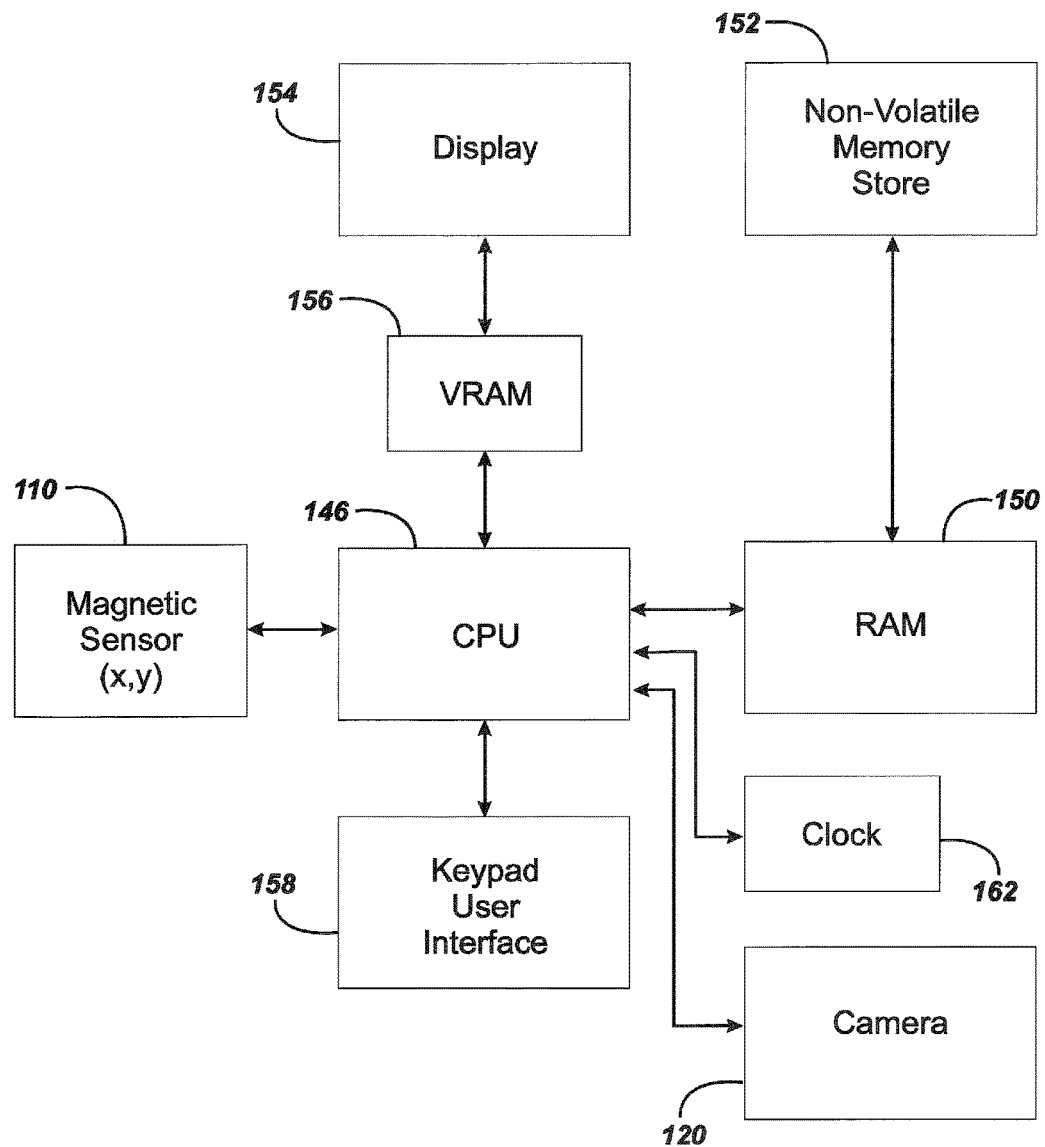
FIG. 9 is a block diagram of an embodiment of the cable counter and overlay management system of the present invention.

Referring to FIG. 8, the PCB 125 carries the logic circuitry and electronics of the counter module 122. An array of nine tact switches 138 is located on the front-facing surface of the PCB 125. The PCB 125 also carries the two-axis magnetic sensor 110, a battery 142 and a twelve pin connector 144. The counter module 122 sends data to the pipe inspection system cable and monitor (not illustrated) through the slip-ring assembly (not illustrated). The keypad 124 (FIG. 4) includes a label placed over the array of tact switches such as 138. The keypad 124 allows an operator to actuate the tact switches 138 to control the display, set the time, set the cable and drum dimensions, set the distance display parameters, set a temporary local zero-point for intermediate measurements, and create and activate text overlays which can be displayed over the camera image on a display 154 (FIG. 9). This capability, for example, enables a commercial user to add text describing the elements in a particular section of pipe to the camera image, and to record the composite image to a portable medium (such as a memory stick, thumb drive or DVD, for example) for record keeping or to provide to a customer. The counter module 122 (FIG. 6) is powered by the power supplied to the pipe inspection system 115, while the battery 142 provides power for a non-volatile memory 152 (FIG. 9) to provide data storage and maintain time and date after power shutdown.

Referring to FIG. 9, keypad inputs are provided from a keypad user interface 158 to a central processing unit (CPU) 146 which may in turn modify a video random-access memory (VRAM) 156 or a system random-access memory (RAM) 150 appropriately. The CPU 146 also exchanges video and control data with the camera unit 120 and may include analog-to-digital conversion of the image stream from the camera unit 120, which may then be combined with overlay data to send a composite image output via VRAM 156 to the display 154. The non-volatile memory 152 allows parameters and overlay data to be preserved between system starts. Magnetic sensor (x, y) data from the two-axis magnetic sensor 110 is provided in digital form to the CPU 146 and integrated into the distance count sent to the display 154. Process timing and system time calculations are based on information from a clock unit 162. The true distance traveled computation is based on the angular measurement from the two-axis magnetic sensor 110 and user parameters such as the inner radius of the cable storage drum 116, the width of the cable storage drum 116, the diameter of the push-cable 118, and the total length of push-cable 118 stored on the cable storage drum 116. These parameters may be loaded into the non-volatile memory 152 during initial configuration in manufacture or modified by the operator when necessary.

In calculating true distance traveled for the camera head 120 (FIG. 5) a correction is necessary to compensate for the fact that the push-cable 118 within the drum is stored around an effective internal diameter that increases as layers of turns of the push-cable 118 unwind, and decreases as layers of turns of the push-cable 118 are run back into the cable storage drum 116. Correcting for true distance traveled can be accomplished using a lookup table interpolation, or by using an empirical curve fit, or a theoretic formula. A parabolic calculation can be used for arriving at an improved true distance traveled by the camera head 120 that includes a packing density estimation factor $\acute{\eta}$ derived from a fit. The correction formula is:

$$L = \frac{c^2 d^2 \pi \acute{\eta} + 4c\pi^2 r^2 - 4\pi w d^2 L'_{max} \acute{\eta}}{w\check{c}}$$

where the variables represent the following parameters and values:

L→cable payout length c→angular counts from sensor, phase unwrapped

č→number of counts per revolution d→cable diameter r→cable drum inner radius w→cable drum width $L_{max}$→total stored cable length $\acute{\eta}$→packing density estimation factor FIGS. 10A-10F present flow-charts of sub-routines within the cable-counter software. The cable counter module 122 interacts with a camera control unit, and other system elements, by data sent across the power-line communication link, or PLC (not illustrated).

Figure 10A:
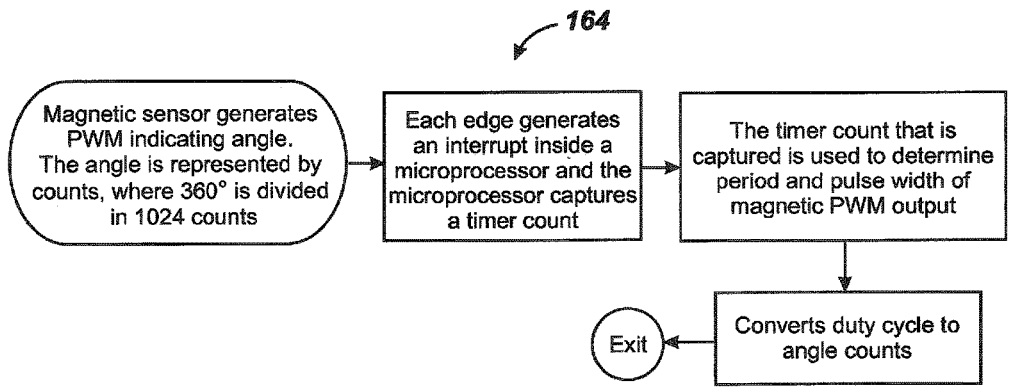
FIGS. 10A-10F are flowcharts illustrating the logic performed in managing data in the illustrated embodiment of the cable counter and overlay management system.

In FIG. 10A, sequence 164 describes the receipt of a PWM signal from the two-axis magnetic sensor 110 (FIG. 7) that is captured by a microprocessor and used to determine angle.

Figure 10B:
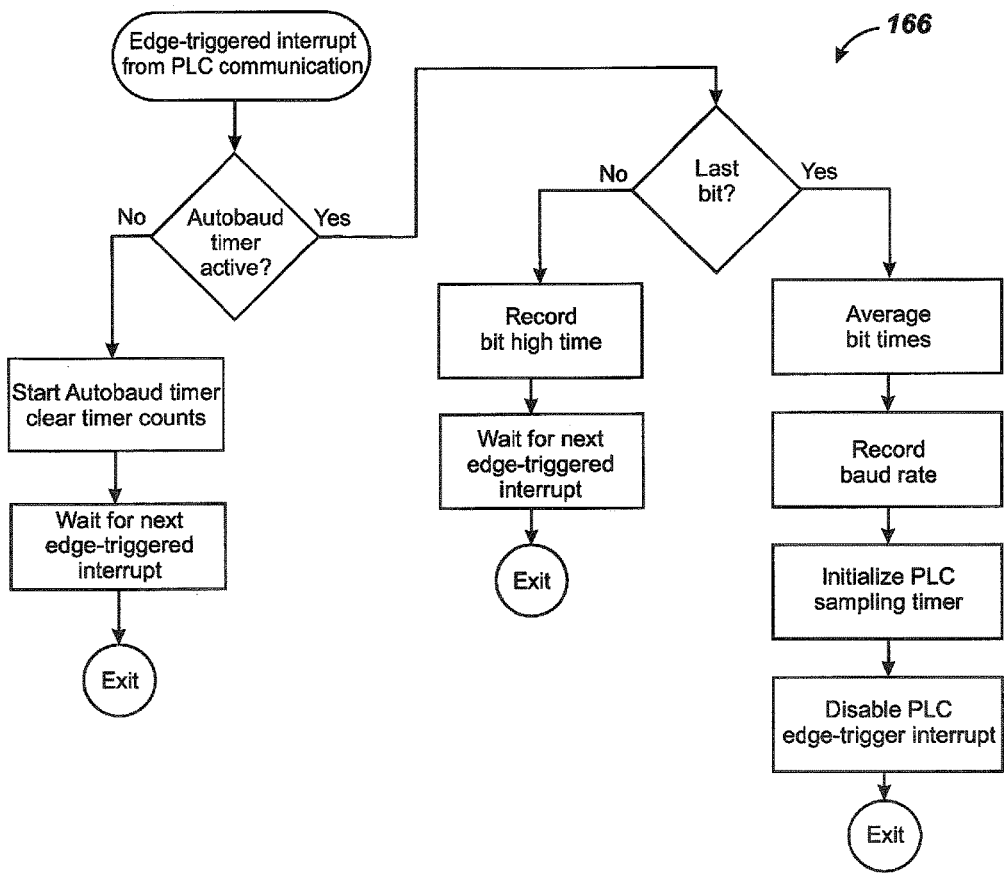

In FIG. 10B, sequence 166 describes the autobaud process used for the power-line communication (PLC) system associated with the camera control and display unit connected to the pipe inspection system. If the autobaud counter is active, and a high and low bit time have not been collected, the bit-time is recorded; otherwise the bit timer is started and the bit counter reset. After both a high true and low time have been collected, the baud rate is computed and recorded. The sampling timer of the power-line communication interface is initialized and the interrupt disabled.

Figure 10C:
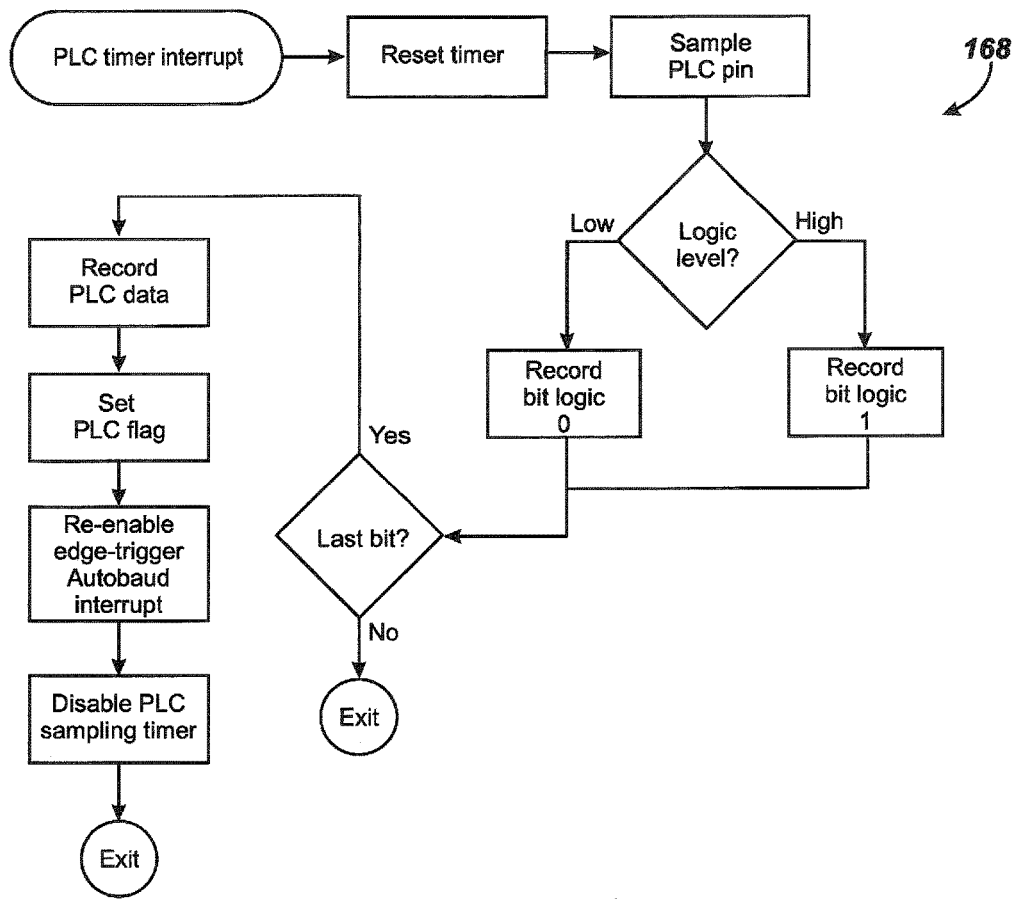

In FIG. 10C, sequence 168 describes the logic of a PLC byte reception. For each PLC timer interrupt the PLC pin is sampled and its bit state recorded. If it is the last bit, the PLC data byte is stored and the sampling timer is disabled.

Figure 10D:
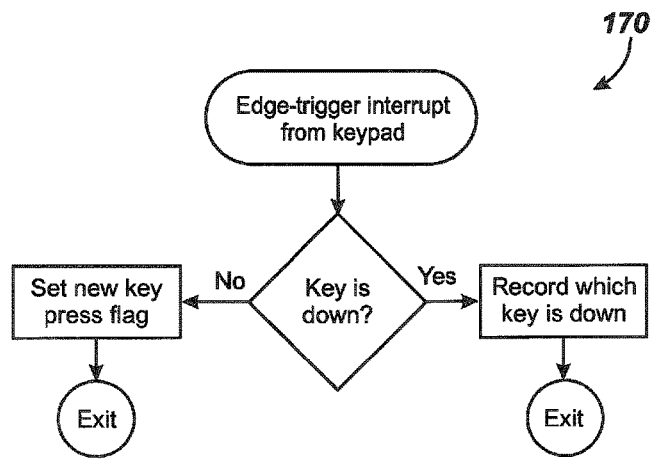

In FIG. 10D, Sequence 170 describes the logic following the receipt of an edgetriggered interrupt from the keypad. The key press received is recorded as either a key pressed and held down or a key pressed and released. In the latter case a key press flag is reset.

Figure 10E:
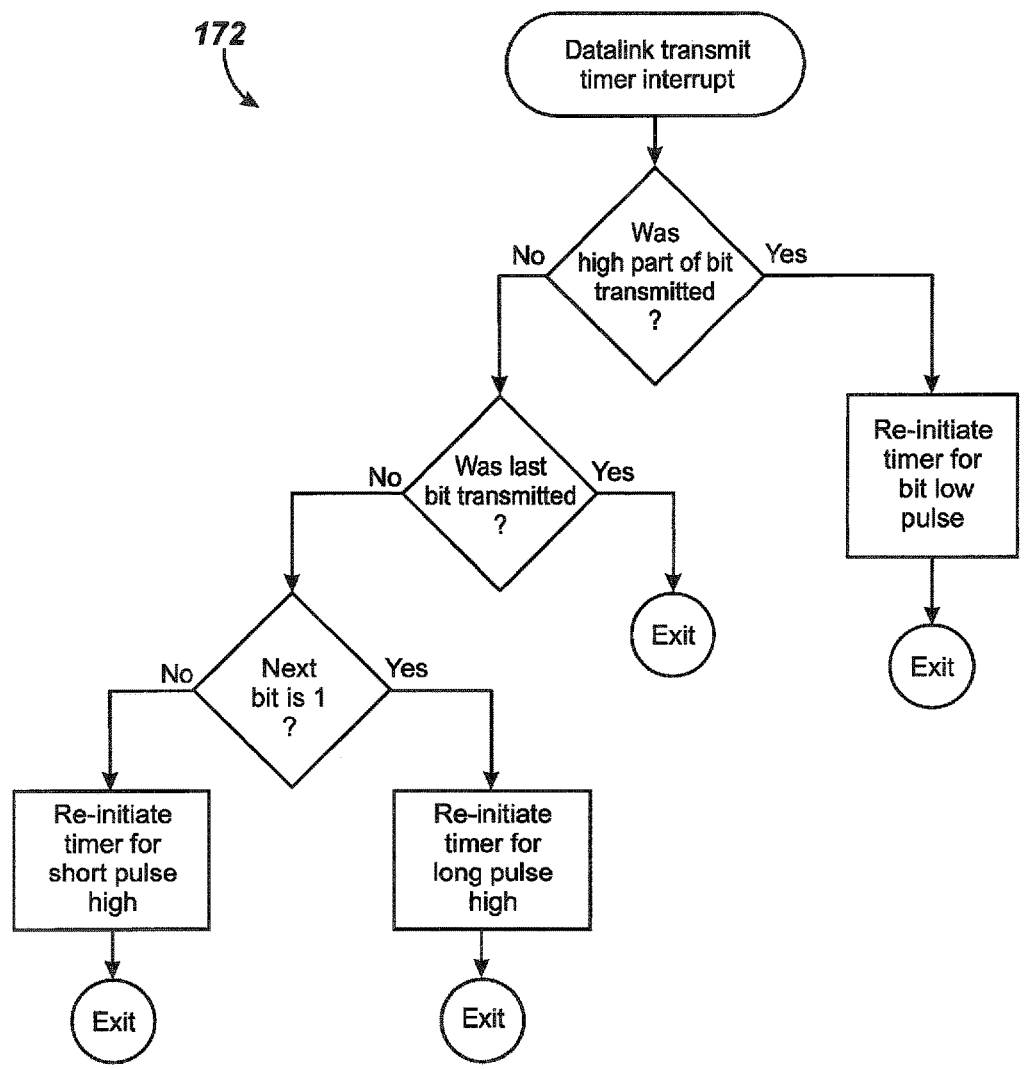

FIG. 10E illustrates the logic sequence 172 when an interrupt is received from a data link transmit timer. This event is used as a signal to time the transmission of count data for example, into the video data stream to create count data on the display. Depending on the logic level of the bit that has to be transmitted the system will re-initialize the data link transmit timer. The data link communication format in general is as follows:

Format
    Start Bit (66% Duty ON)
    Address Byte 3-Bits→'From' Node
        3-Bits→'To' Node 2-Bits→Message Type
    Data Bytes 1-15
    Stop Bit (33% Duty ON)

Figure 10F:
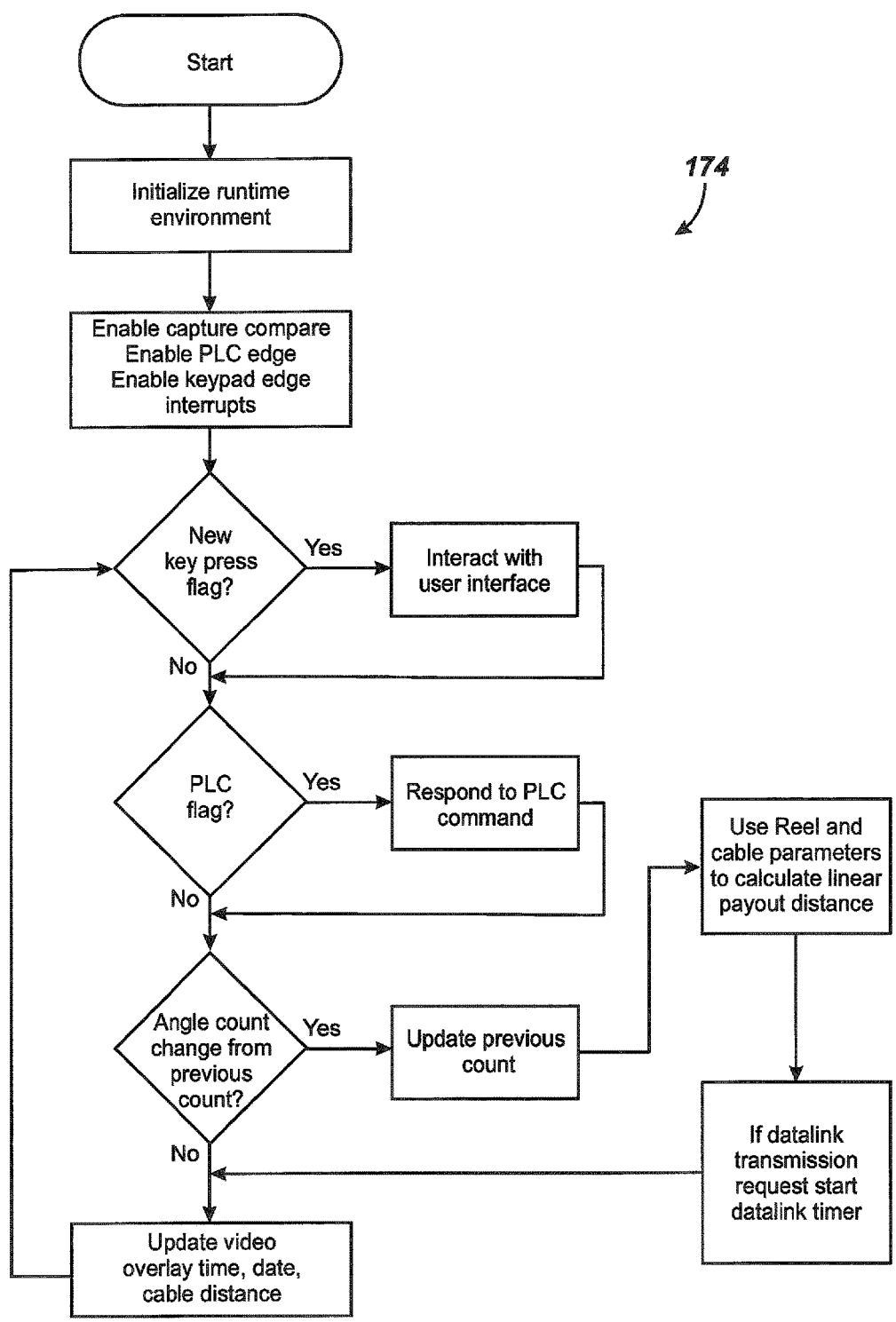

In FIG. 10F, sequence 174 describes the overall coordination of the runtime environment and preparation for receipt of key press, PLC flags, new angle count data, and coordinated video updates. Depending on the interrupts received, the system interacts with the key-pad user interface, responds to PLC commands, recalculates distance data using stored parameters, readies the data link transmit and updates video overlays with time, date and cable distance data. The data link data is transmitted using a particular data format as shown in the following table;

| Type | Byte | Value | Meaning |
| --- | --- | --- | --- |
| Count | 1 | 0x80 | Count Message ID |
| Information (cm) | 2-5 | 0-xxx | Count (cm) |
|  | 6 | 0x0-0xFF | Checksum |
| Raw Count | 1 | 0x81 | Raw Count Message ID |
| Information | 2-5 | 0-xxx | Power On Count |
|  | 6-9 | 0-xxx | Temp Zero Count |
|  | 10-13 | 0-xxx | Current Count |
|  | 14 | 0x0-0xFF | Checksum |
| Measurement | 1 | 0x82 | Measurement Origin Message ID |
| Origin | 2 | 0 or 1 | Power On, Absolute or Relative Count State |
|  | 3 | 0x0-0xFF | Checksum |
| Odometer | 1 | 0x83 | Odometer Message ID |
| Information | 2-5 | 0-xxx | Odometer Count (cm) |
|  | 6 | 0x0-0xFF | Checksum |
| Reel Information | 1 | 0x84 | Reel Info ID |
|  | 2-4 | 0-xxx | Cable Length (ft) |
|  | 5 | 0x00-0x02 | Reel Type |
|  | 6 | 0x00-0x02 | Cable Type |
|  | 7 | 0x0-0xFF | Checksum |
| Raw Total Count | 1 | 0x85 | Raw Count Message ID |
| Information | 2-5 | 0-xxx | Total Sum Raw 32-Bit Count |
|  | 6 | 0x0-0xFF | Checksum |
| "Count Plus" | 1 | 0xF0 | Software Version Message ID |
| Software Version | 2-5 | 0-xxx | Software Version |
|  | 6 | 0x0-0xFF | Checksum |

Figure 11:
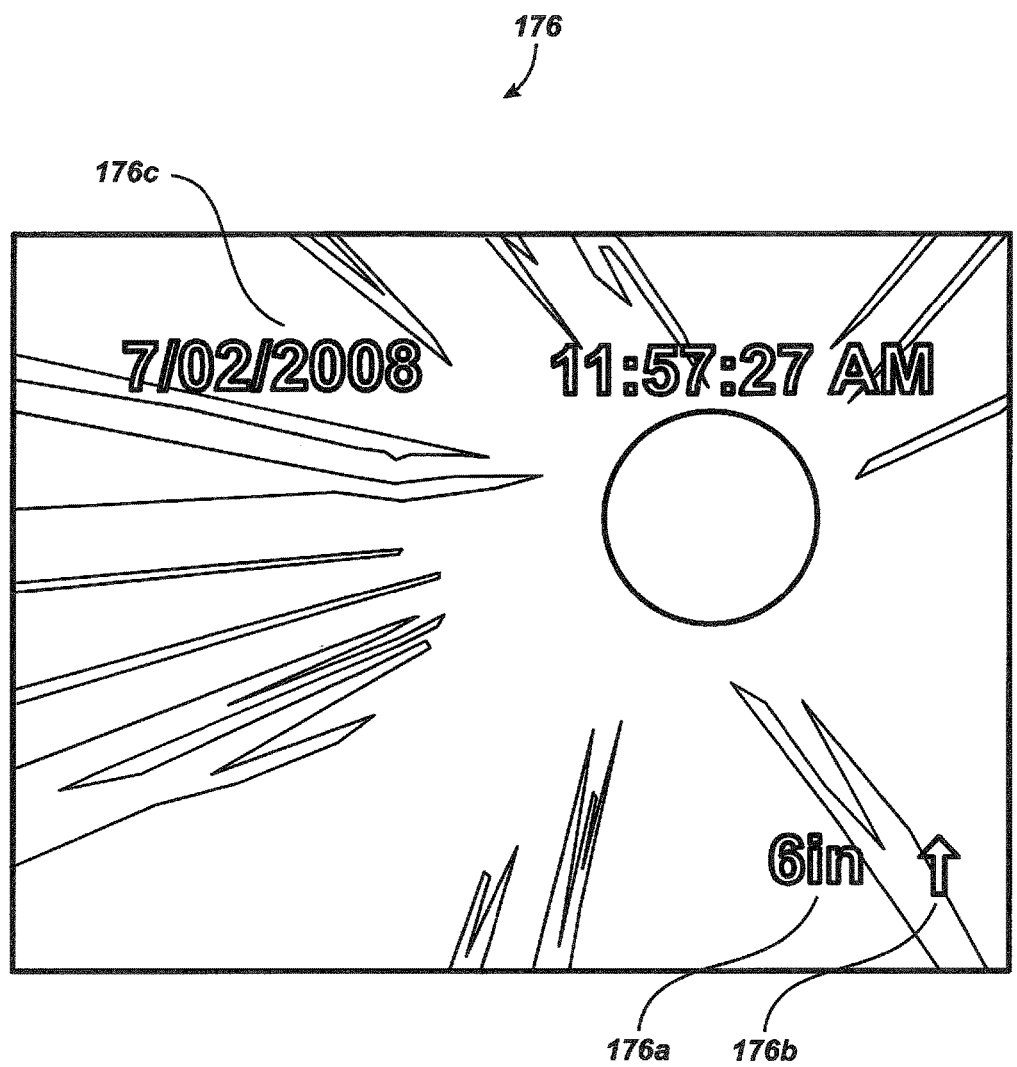
FIG. 11 illustrates a typical screen display of distance counting using the system of FIG. 9.

Referring to FIG. 11, a typical display image 176 of distance counting during the inspection of pipe includes both the current distance count 176a (here, 6 inches) and direction of travel 176b (out from the cable storage drum 116 as indicated by the arrow icon) are displayed, as are system time and date 176c.

Figure 12:
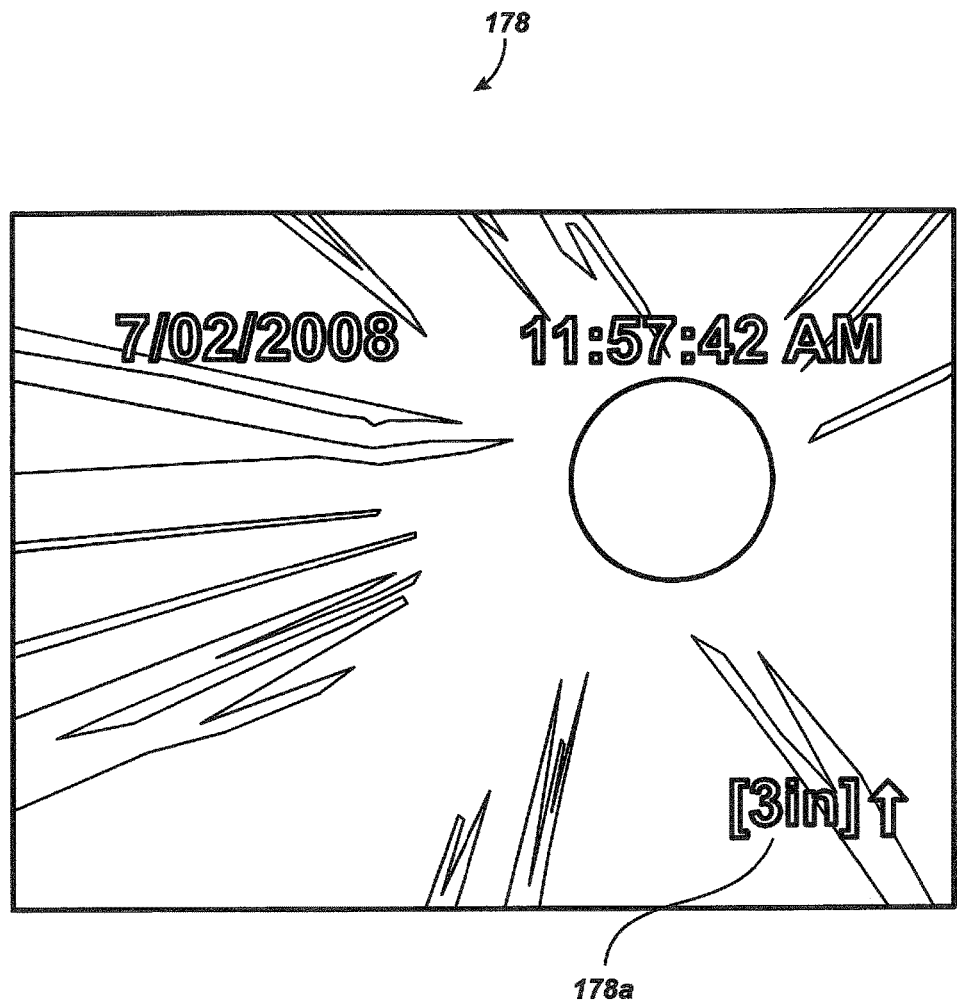
FIG. 12 illustrates a typical screen display using the system of FIG. 9 to establish a separate distance count from a user-selected point such as the beginning of a pipe segment.

Referring to FIG. 12, a typical display image 178 includes a separate distance count 178a from a user-selected point, such as the beginning of a pipe segment. The distance count 178a illustrated in FIG. 12 is bracketed, indicating it is a separate count from the main distance count, and that it was started at a user-defined "local zero-point." Such a local zero-point, for example, might be at the head of a pipe that was some distance from the reel due to the configuration of the work site.

Figure 13:
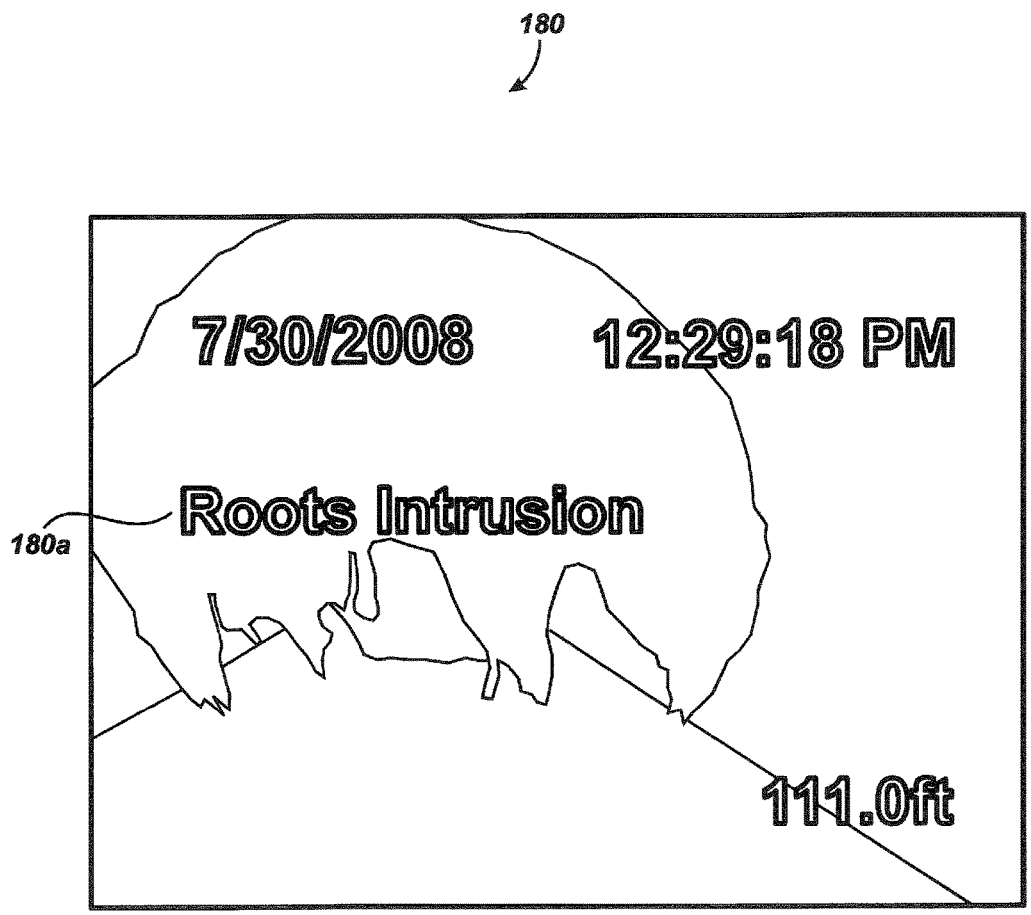
FIG. 13 illustrates a typical text overlay displayed for identification of detected features in a pipe using the system of FIG. 9.

Referring to FIG. 13, a typical display image 180 includes a typical text overlay 180a displayed for identification of detected features in a pipe using the present invention. The custom-created text "Roots Intrusion" illustrated in FIG. 13 has been selected to be overlaid onto the display for the purpose of labeling the feature in the image where roots have entered a pipeline under inspection. A vocabulary of user-selectable stored strings can be pre-programmed into non-volatile memory. Such a vocabulary for a pipe inspection system might include, for example, labels for:
1. Property line cleanout
2. 2-way cleanout
3. Septic tank
4. Roots intrusion
5. Offset
6. Belly
7. Crack
8. Collapsed/crushed
9. Bottom compromised
10. Foreign object/blockage
11. Wye
12. Test wye
13. Combo
14. Sanitary tee
15. Transition material
16. Transition-size.

Figure 14:
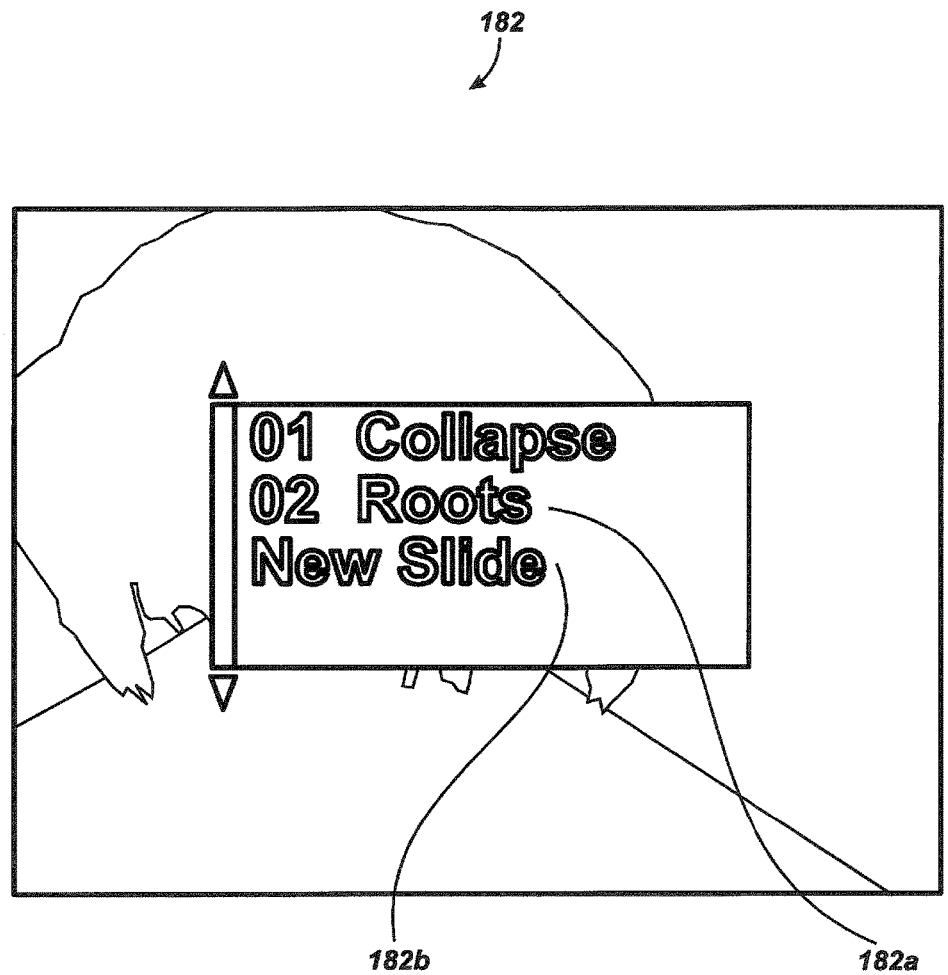
FIG. 14 illustrates a display image showing a typical overlay selection process from a stored series of user-defined text overlays.

FIG. 14 illustrates a display image 182 of a typical overlay selection process from a stored series of user-defined text overlays. Two existing stored overlays 182a are listed as "01" and "02" which can be chosen (by user keypad presses) to be displayed over the camera image. Additionally in FIG. 14, a "New Slide" option 182b is listed to create a new overlay slide. Slide text can be created by choosing characters from a screen display of all characters and composing the text overlay by selecting them one at a time.

The illustrated embodiments can be modified with a keyboard enabling more rapid character input, or some other input method such as voice recognition, touch-screen selections, or handwriting recognition with a digitizing tablet can be used.

Alternate embodiments of the present invention can be used to adapt the invention to any device requiring the detection of angular motion, such as a flywheel device, for example, a governor, or a vehicle wheel. For example, pipe-cleaning, drilling, or cable-laying systems could incorporate the cable counter of the present invention. The cable counter of the present invention can also be readily retro-fitted to existing pipe inspection, pipe-cleaning, drilling and cable-laying systems.

In general terms, at least two permanent magnets are mounted in spaced apart fashion, on either a frame, or a rotatable member supported on the frame for rotation about an axis. A magnetic sensor is mounted on the other one of the rotatable member or frame on which the magnets are not mounted, so that either the magnets rotate around the magnetic sensor or the magnetic sensor rotates between the permanent magnets. The frame could be any frame, such as a planar element or other structural piece of an apparatus, and not a tubular support frame. The purpose of using two identical spaced apart magnets is to create a super-position composite magnetic field that provides a field that does not have a large curvature. The field lines are not highly curved in the annular zone around zone around the axle 134. The field intensity does not vary to an extreme degree as the two spaced apart magnets 128 and 130 are rotated around the fixed two-axis magnetic sensor 110. The magnets 128 and 130 are spaced far enough apart so that neither magnet passes too close to the magnetic sensor 110 as they rotate around the axle 134. For optimal results the radius of the permanent magnet offset distance from the axis of rotation is preferably greater than about one and one-half times the radial offset distance d (FIG. 2) from the center of the magnetic sensor 110 and the axis of rotation. More preferably this proportional ratio is greater than about two.

Clearly, other embodiments and modifications of the present invention will occur to those skilled in the art, in view of these teachings. Therefore, the protection afforded the invention is to be limited only by the following claims, which include all such embodiments and modifications when viewed in conjunction with the above specification and accompanying drawings.

We claim:

1. A pipe inspection cable counter and overlay management system, comprising:
   a deployable cable;
   a camera head coupled to the deployable cable;
   an apparatus for detecting angular motion about an axis for use in determining cable deployment distance, comprising:
   a rotatable member for storing the deployable cable;
   an axle supporting the rotatable member for rotation about an axis;
   a frame supporting the axle;
   a microprocessor;
   a multi-axis magnetic sensor mounted on one of the frame and the rotatable member at a predetermined offset distance below a central axis of the axle, the multi-axis magnetic sensor having an output operatively coupled to the microprocessor that generates signals representing changes in a magnetic field in at least two orthogonal axes (x, y);
   at least a pair of permanent magnets mounted in a spaced apart relationship on the other one of the frame and rotatable member to generate, during relative rotational movement between the magnetic sensor and the magnets, a distributed composite magnetic field centered around an axis of rotation of the rotatable member; wherein the multi-axis magnetic sensor detects changes in the generated composite magnetic field in the at least two orthogonal axes (x, y) and provides output information related to the change in composite magnetic field to a microprocessor, and wherein the microprocessor determines information about deployment of the deployable cable based on the information related to the change in composite magnetic field; and
   a display for providing a visual output based on signals from the camera head.

2. The system of claim 1, wherein the rotatable member comprises a cable storage drum.

3. The system of claim 1, wherein the magnetic axes of the magnets pass substantially through the axis.

4. The system of claim 1 wherein the North pole of one of the magnets opposes the South pole of the other one of the magnets.

5. The system of claim 1 wherein the magnetic sensor includes a plurality of Hall effect devices.

6. The system of claim 1 wherein the magnets are cylindrical.

7. The system of claim 1 wherein a determined distance count of cable deployment are provided on the display.

8. The system of claim 1 wherein a determined distance count of cable deployment from a user-selected point is provided on the display.

9. The system of claim 1 wherein a determined direction of travel of cable deployment is determined in the microprocessor based at least on the magnetic sensor output information and provided on the display.

10. The system of claim 1, wherein a text overlay identifying detected features in a pipe is provided on the display.

11. The system of claim 10, wherein a plurality of text overlays are stored in a memory of the system.

12. The system of claim 11, wherein one or more of the plurality of text overlays are user-defined overlays.

13. The system of claim 1, wherein the magnetic sensor senses the composite magnetic fields in three orthogonal axes (x, y, z).

14. The system of claim 1, wherein the display provides the information about deployment of the deployable cable.

15. The system of claim 1, wherein the information related to the change in composite magnetic field provided by the magnetic sensor comprises a pulse width modulation (PWM) indication angle and wherein the microprocessor converts the PWM indication angle to an angular counts (c).

16. The system of claim 15, wherein the angular counts (c) are converted to a distance measurement based on predefined reel and cable parameters.

* * * * *